United States Patent [19]

Richman

[11] B 4,001,212

[45] Jan. 4, 1977

[54] MACROCYCLIC POLYAMINES
[75] Inventor: Jack E. Richman, Wilmington, Del.
[73] Assignee: E. I. Du Pont de Nemours and Company, Wilmington, Del.
[22] Filed: Oct. 3, 1973
[21] Appl. No.: 403,326
[44] Published under the second Trial Voluntary Protest Program on March 23, 1976 as document No. B 403,326.
[52] U.S. Cl. .................. 260/239 BC; 260/30.4 EP
[51] Int. Cl.² ........................................ C07D 259/00
[58] Field of Search ............................ 260/239 BC

[56] References Cited
UNITED STATES PATENTS 1,951,992  3/1934  Perkins ................. 260/239 BC X

OTHER PUBLICATIONS

Chemical Substance Index, *Chemical Abstract*, vol. 76, p. 1687CS, (1972).

*Primary Examiner*—R. Gallagher
*Assistant Examiner*—D. B. Springer

[57] ABSTRACT

Macrocyclic polyamines containing 3–7 nitrogen atoms in the ring and destablized to complex formation by (1) an asymmetric ring and/or (2) provision of nitrogen atoms in excess of that required for complex formation are described. The compounds can be used to extract metal ions from solution. The metal complexes are thermally activated curing agents for epoxy resins.

7 Claims, No Drawings

MACROCYCLIC POLYAMINES

BACKGROUND OF THE INVENTION

1. Field of the Invention

This invention relates to novel macrocyclic polyamines and their complexes with selected metals.

2. The Prior Art

H. Koyama and T. Yoshino, *Bull. Chem. Soc. Japan* 45, 481 (1972) have reported the synthesis of triaza macrocycles wherein the nitrogen atoms are separated by bridges of 2 or 3 methylene groups.

Tetraaza macrocycles have been described by H. Stetter and K.-H. Mayer, *Chem. Ber.*, 94, 1410 (1961) and by H. Stetter and E. E. Roos, ibid, 87, 566 (1954) when at least two of the bridges joining the nitrogen atoms are of 2 methylene units in length.

Cyclic trimer, tetramer, pentamer, hexamer and heptamer of hexamethylenediamine have been described by H. Zahn and H. Spoor, *Chem. Ber.*, 92, 1375 (1959).

G. Schreiber, W. Schreiber and W. Lautsch have described C-benzyl substituted hexaaza macrocyclic compounds, *Chem. Ber.*, 98, 2765 (1965), while C-methyl and phenyl substituted compounds have been described by E. K. Barefield and D. H. Busch, *Inorg. Chem.*, 10, 1216 (1971) and by R. Sarfati, M. Pais and F. X. Jarreau, *Bull. Soc. Chim. Fr.*, 255 (1971).

Unsaturated tetra- and pentaaza-macrocyclic compounds have been described by J. B. Thompson in U.S. Pat. No. 3,485,818 issued Dec. 23, 1969.

SUMMARY OF THE INVENTION

The present invention is directed to novel compounds which have the formula:

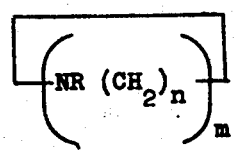

where R is H or p-toluenesulfonyl;
$m$ is 3-7
and each $n$ is independently 2-5 with the provisos that:
where $m = 3$ and two of the $n$ are 2 or 3 then the third $n$ is 4 or 5; and
when $m$ is 4 and one $n$ is 2, the remaining values of n are 3, 4 or 5.

This invention also includes complexes of the above amines where $R = H$ with metals of groups VI $b$, VII $b$, VIII, I$b$ and II$b$ of the Periodic Table, and in particular complexes of the aforesaid polyamines with copper, zinc, and nickel.

DETAILED DESCRIPTION OF THE INVENTION

Macrocyclic polyamines which form stable complexes with metal ions are known. The present invention is directed to macrocyclic polyamines in which complex formation is hindered by (1) asymmetric distribution of nitrogen atoms in the ring, and/or (2) the provision of nitrogen atoms in excess of that required for stable complexation. The destabilized complexes can be employed to generate free amine thermally and are hence thermally activated initiators for the curing of epoxy resins.

The macrocyclic amines of the present invention can be made by condensation of a suitable di-terminal amine sulfonamide alkali metal salt with a di-terminal halide or a di-terminal sulfonate ester in a polar aprotic solvent. The reaction is preferably carried out at 50°C to 120°C.

Preferred solvents are dimethylformamide and dimethylsulfoxide.

The preferred alkali metal salts are sodium salts of the di-terminal amine sulfonamides. Using the preferred metal salts, it is not necessary to employ high dilution techniques to obtain good yields of product. Preferred concentration of the alkali metal salts (and of the di-terminal dihalide and di-terminal sulfonate ester) in the above solvents is 0.05-0.5 mole/liter.

The products formed by the above reaction are the N-toluenesulfonamide (N-tosyl) derivatives of the macrocyclic polyamines. These products can be hydrolyzed to the parent amines by warming a 20% solution of the tosyl derivative in 97% sulfuric acid at 95°–100°C until a sample gives a clear solution in alkaline water, generally about 1–48 hours. Dilution of the reaction mixture with ether yields the dihydrosulfate salts which can be converted to the free base or, for the purpose of characterization, to the hydrochloride salts, by treatment with ion-exchange resin.

Metal complexes of the above amines can be prepared by treating a solution of the hydrochloride or dihydrosulfate salts with a stoichiometric amount of the metal salt. The mixture is neutralized and evaporated. The metal complexes can be separated from inorganic residue by extraction and recrystallized from organic solvents or from water.

UTILITY

The macrocyclic polyamines of the present invention can be employed to extract metals from solutions. The complexes formed are generally less stable e.g., to acid, than the complexes of amines of the prior art, which facilitates recovery of the extracted metal.

The metal complexes are useful as thermally activated curing agents for epoxy resins.

EMBODIMENTS OF THE INVENTION

The following examples illustrate specific embodiments of the invention. Melting points are in °C unless otherwise specified. The abbreviation "tosyl" (Ts) refers to the p-toluenesulfonyl radical, p-$CH_3C_6H_4SO_2$. Tosyl derivatives of amines and alcohols can be prepared by the procedure described below for the preparation of N,N-bis(2-p-toluenesulfonamidoethyl)-p-toluenesulfonamide, an intermediate used for the preparation of the product of Example 1.

EXAMPLE 1

1,4,7-Triazacyclododecane

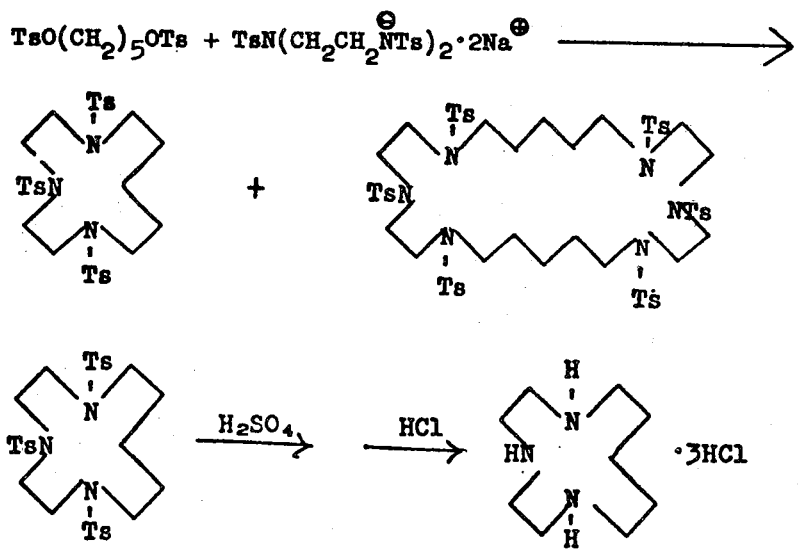

A solution of 25 mmol (15.2 g) of the disodium salt of N,N-bis(2-p-toluenesulfonamidoethyl)-p-toluenesulfonamide in 250 ml of commercial dimethylformamide (DMF) was stirred at 95°–100° while a solution of 25 mmol (10.3 g) of the di-p-toluenesulfonate ester of 1,5-pentanediol in 75-125 ml of DMF was added over a 3-hour period. Heating was continued for 1 hour, the mixture was cooled and water was added until the mixture approached the cloud point (DMF or ethanol can be added to clear the cloudy solution if necessary). The product slowly crystallized and was washed with ethanol, weight 11.1 g (70% crude yield). This solid was shown by thin layer chromatography (tlc) on silica with 2% ethanolic chloroform to be a mixture of two uv active components, the major product, the tritosyl derivative of 1,4,7-triazacyclododecane, being eluted ahead of the minor component, the hexatosylamide of 1,4,7,13,16,19-hexaazacyclotetracosane.

The crude solid was refluxed in 50 ml of ethanol with addition of chloroform until a milky suspension resulted. The solid was filtered off to give a 15% yield of the hexatosyl derivative of 1,4,7,13,16,19-hexaazacyclotetracosane, mp 170.5–172°. This product was readily recrystallized from pyridine to give a 1:1 solvate, mp 204°–205°C.

Anal. Calcd for $C_{60}H_{78}N_6S_6O_{12} \cdot C_5H_5N$: C, 57.97; H, 6.21; N, 7.28; S, 14.29. Found: C, 58.04; H, 6.30; N, 7.24.

Vacuum drying of this solvate (130°/0.1 mm) removed the pyridine to leave the unsolvated compound, mp 210°–211.5°. IR (KBr): 3.38, 6.24, 6.68, 6.84, 7.44 (st), 7.66 (sh), 7.75 (sh), 8.46, 8.64 (st), 8.95, 9.18, 9.82, 12.28, 13.75 (b), and 14.35 (b) $\mu$. Proton NMR ($CF_3CO_2H$) showed tosyl signals (42H, $CH_3$ width at ½ height~ 3 HZ), 3.0–3.6 ppm (m, 24H), and 1.1–2.0 (broad, 12H).

Anal. Calcd for $C_{60}H_{78}N_6S_6O_{12}$: C, 56.85; H, 6.20; N, 6.63; S, 15.17; MW, 1267.7. Found: C, 56.85; H, 6.10; N, 6.70; S, 14.98; MW ~1000 (ebullioscopic in pyridine).

The major product, the tritosyl derivative of 1,4,7-triazacyclododecane was obtained by concentration of the ethanol-chloroform filtrate after separation of the hexatosylamide of 1,4,7,13,16,19-hexaazacyclotetracosane. After recrystallization from ethanol-chloroform, the tritosylamide of 1,4,7-triazacyclododecane melted at 172°–173°C. IR (KBr): 3.40, 3.47, 6.23, 6.68, 6.87, 7.48 (b, st), 7.64 (sh), 8.45, 8.63, 8.94, 9.18, 9.62, 10.08, 10.29, 10.54, 10.96, 11.23, 11.90, 12.27, 14.10, and 14.50 (b) $\mu$. Proton NMR ($CF_3CO_2H$) showed tosyl signals (21H, $ArCH_3$ width at 1/2 height ~4 Hz), 3.1–3.6 (12H, spike at 3.44 ppm), and 1.71 ppm (6H, broad m).

Anal. Calcd. for $C_{30}H_{39}N_3S_3O_6$: C, 56.85; H, 6.20; N, 6.63; S, 15.17; MW, 633.8. Found: C, 55.90; H, 6.00; N, 6.18; S, 14.50; MW 735–760. (ebullioscopic in pyridine).

This sample contained a trace of chloroform, identified in the mass spectrum, which accounts for the low analyses.

A solution of 22.2 g of the tritosylamide of 1,4,7-triazacyclododecane, prepared as described above, in 50 ml of concentrated sulfuric acid was heated for 22 hours at 100°, at which time a sample gave a clear solution in water made basic with sodium hydroxide. To the acid mixture was added 125 ml of anhydrous ether with cooling. The hygroscopic dihydrosulfate salt precipitated and was filtered and washed with ether under nitrogen, weight 18.5 g (~75% pure by elemental analysis, 17.65% C, theoretical 23.23% C). This represents an 86% yield of the salt of 1,4,7-triazacyclododecane. A 5.5-g sample was ion-exchanged on a column of 100 ml of Dowex 2X8 (chloride form, 1.2 meg/ml, 200–400 mesh) and concentrated leaving 2.9 g of solid. 1,4,7-Triazacyclododecane trihydrochloride was recrystallized from aqueous methanol, weight 1.25 g, mp 230° (slow dec), 259°–268° (gas evolution). IR (KBr): 3.3–4.3 (broad tailing peak), 6.19, 6.29, 6.73, 6.82, 6.91, 7.1, 7.31, 7.4, 7.8, 8.21, 8.87 (w), 9.1, 9.39, 9.63, 9.92, 10.23, 10.55, 11.12, 11.65, 12.45, 12.86, 13.05, and 14.05 $\mu$.

NMR ($D_2O$, $H_2SO_4$ salt): 1.7 (m, 6H), 3.2, 3.37 (t and s, 12H), and 4.78 ppm (s, exchange). Anal. Calcd for $C_9H_{24}N_3Cl_3$: C, 38.51; H, 8.62; N, 14.97; Cl, 37.90. Found: C, 38.31; H, 8.46; N, 14.98; Cl, 38.09, 37.89 (ionic).

The disodium salt of N,N-bis(2-p-toluenesulfonamidoethyl)-p-toluenesulfonamide required in the above synthesis was prepared as follows:

In a 1-liter flask a mixture of 190 g of commercial toluenesulfonyl chloride and 500 ml of reagent grade pyridine was heated to 50° while 35 g of commercial diethylenetriamine in 50 ml of pyridine was added maintaining 50°–60° throughout and for 0.5 hour after addition was completed. The mixture was cooled and treated with 300–400 ml of water. Crystallization overnight gave 132 g of white solid N,N-bis(2-p-toluenesulfonamidoethyl)-p-toluenesulfonamide, mp 173°–174°, after washing with ethanol. Additional crops from the mother liquor gave 21 g of product, total yield 153 g (80%). This material was sufficiently pure after drying for conversion to the disodium salt with sodium ethoxide. An analytical sample was obtained by recrystallizing the product from acetonitrile, mp 172°–173.5°. IR (KBr): 3.06, 6.24, 6.79, 6.9 (b), 7.55 (b, st), 7.66, 7.75, 8.65 (b, st), 9.17, 9.82, 10.09, 10.66 (w), 11.02 (w), 12.3 and 13.4–15 μ (broad bands).

NMR (CDCl$_3$): δ 7.9–7.2 (m, 7, aromatic), 5.53 (2, broad s, NH), 3.13 (m, 8, CH$_2$), and 2.42 (s, 9, CH$_3$). Anal. Calcd. for $C_{25}H_{31}N_3S_3O_6$: C, 53.08; H, 5.52; N, 7.43; S, 17.00. Found: C, 52.98; H, 5.28; N, 7.56.

The disodium salt was prepared by treating a stirred boiling suspension of 132 g of the sulfonamide in 1 liter of ethanol with 500 ml of sodium ethoxide solution (from 11.2 g of sodium) over a 10 minute period. The solution became homogeneous and it was cooled to 25° and seeded. Large colorless crystals of the salt were filtered and washed under nitrogen, weight 136.5 g (96% yield). IR (KBr) similar to the parent compound minus 3.06 band and with 9.17 band split to 8.94 and 9.31.

EXAMPLE 2

1,4,7,13,16,19-Hexaazacyclotetracosane

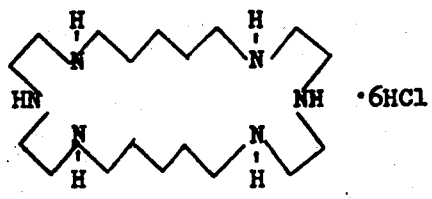

The hydrolysis of 3.6 g of the hexatosylamide of 1,4,7,13,16,19-hexaazacyclotetracosane was carried out as described in Example 1 to give the dihydrosulfate salt as a waxy solid. Ion exchange of this salt as described in Example 1 gave a solution of the hexahydrochloride salt. Addition of methanol gave 1.0 g of 1,4,7,13,16,19-hexaazacyclotetracosane hexahydrochloride, mp 280° (dec). IR (KBr): 2.94, 3.37, 3.6–4.3 (broad bands), 6.31, 6.82, 6.92, 7.19, 7.48 (w), 7.65 (w), 7.84 (w), 8.3–10 (broad peak max. 9.35), 10.1, and 11.9–13.7 μ (multiple bands). NMR (D$_2$O): 1.7–2.2 (m, 12H), 3.33 (t, 8H), 3.71 (s, 16H), and 4.86 ppm (broad s, exhange).

Anal. Calcd for $C_{18}H_{48}N_6Cl_6$: C, 38.51; H, 8.62; N, 14.97; Cl, 37.90. Found: C, 38.80; H, 8.63; N, 14.71; Cl, 38.24.

EXAMPLE 3

1,4,7,10,13-Penta-p-toluenesulfonyl-1,4,7,10,13-pentaazacyclopentadecane

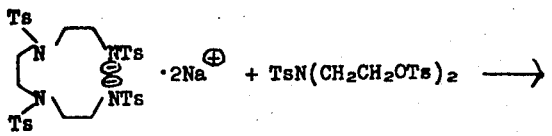

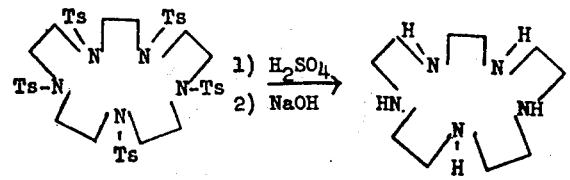

The reaction of TsN(CH$_2$CH$_2$OTs)$_2$ and TsN(CH$_2$CH$_2$NTs)$_2$CH$_2$CH$_2$NTs.2Na on a 0.02 mole scale in DMF using the procedure outlined in Example 1 gave 13.3 g (62.5% yield) of solid product. Proton nmr analysis showed the product to be a 1:1 solvate of the pentatosyl derivative of 1,4,7,10,13-pentaazacyclopentadecane and DMF, mp 270°–278°. Recrystallization of this solvate from DMF-water, followed by drying the solid at 80° (0.1 mm), gave the purified 1:1 solvate. Further drying of this product at 140° (0.1 mm) gave the DMF-free compound, mp 278°–280° (darkening).

IR(KBr): 3.49, 6.25, 6.68, 6.85, 7.43 (b, st), 7.67, 7.77, 8.64 (st), 9.17, 10.25 (b), 12.28 (b), 12.8 (b) and 13.4–14.3μ (4 bands, w). NMR (CF$_3$CO$_2$H): tosyl signals (35H, CH$_3$ w at h/2 = 3 Hz), and 3.37 ppm (s, 20H, w at h/2 = 7 Hz).

Anal. Calcd for $C_{48}H_{62}N_6S_5O_{11}$ (solvate): C, 54.42; H, 5.90; N, 7.93; S, 15.13. Found: C, 54.16; H, 5.75; N, 8.00.

Anal. Calcd for $C_{45}H_{55}N_5S_5O_{10}$: C, 54.82; H, 5.62; N, 7.10; S, 16.23. Found: C, 54.58; H, 5.68; N, 7.25; S, 16.04.

A 58.3-g sample of the pentatosyl derivative of 1,4,7,10,13-pentaazacyclopentadecane prepared as described was dissolved in 120 ml of concentrated sulfuric acid and the solution heated at 100° for 4 hours, at which time a sample gave a clear solution in water made basic with sodium hydroxide. The product was precipitated by the addition of 300 ml of ether, and the off-white solid separated by filtration (nitrogen atmosphere). The solid was slurried in 100 ml of water and 75 ml of 50% sodium hydroxide solution was added to effect separation of an oil. The mixture was continuously extracted with benzene, the benzene layer separated and the solvent evaporated to leave 7.15 g of 1,4,7,10,13-pentaazacyclopentadecane, mp 92°–103°. The product was purified by sublimation at 90°–95° (5μ), and it was obtained in the form of long white electrostatic needles (5.0 g). The solid is hygroscopic.

Anal. Calcd for $C_{10}H_{15}N_5$: C, 55.78; H, 11.70; N, 32.52 Found: C, 54.74; H, 11.16; N, 32.52.

EXAMPLE 4

1,4,7,10,13,16-Hexaazacyclooctadecane

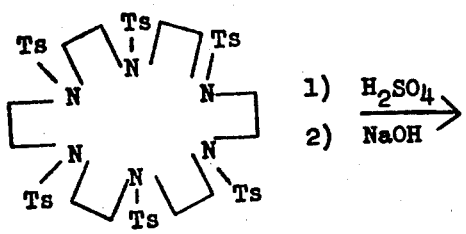

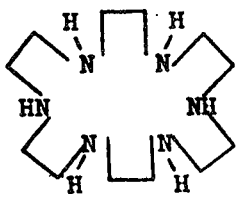

The above reaction was carried out on the 0.01 mole scale in DMF using the procedure outlined in Example 1 to give 7.1 g (60% yield) of the hexatosylamide of 1,4,7,10,13,16-hexaazacyclooctadecane, mp 296° (dec). Recrystallization of the product from DMF by addition of water gave needles, mp 311°–313°. IR (KBr): 3.41, 6.26, 6.69, 6.87, 7.45 (b, st), 7.66, 8.65 (b, st), 8.95 (w), 9.18, 9.35 (w), 9.62 (w), 10.25 (b), 12.3, 13.5 (b), 14.04 and 14.4 μ.

NMR (CF$_3$CO$_2$H): tosyl signals (42H, C$\underline{H}_3$, w at h/2 = 3 Hz), and 3.43 ppm (broad s, 24H, w at h/2 = 7 Hz). 13C NMR (CF$_3$CO$_2$H): 22.39 (CH$_3$), 51.84 (CH$_2$), and 129.62, 132.81, 135.72 and 149.10 ppm (Ar).

Anal. Calcd for C$_{54}$H$_{66}$N$_6$S$_6$O$_{12}$: C, 54.82; H, 5.62; N, 7.10; S, 16.23; MW 1183.6. Found: C, 55.61; H, 5.91; N, 7.17; MW 1100 (ebullioscopic in DMF).

A 21-g sample of the hexatosylamide, prepared as described above, was hydrolyzed with concentrated sulfuric acid to remove the tosyl groups as described in Example 1. Hydrolysis was carried out at 100° for 5.25 hours. The precipitated hexadihydrosulfate salt of 1,4,7,10,13,16-hexaazacyclooctadecane was obtained as a white solid, ~93% pure, 15.2 g. NMR (D$_2$O, hexa-H$_2$SO$_4$ salt): 3.66 (s) and 4.92 ppm (s, exchange).

A 10-g sample of this salt was stirred into 300 ml of boiling water and 5.24 g of the tris-dihydrosulfate salt of 1,4,7,10,13,16-hexaazacyclooctadecane precipitated (96% overall yield from the hexatosylamide). IR (KBr): 3.2–4.3 (broad tailing peak), 6.17, 6.25, 6.58, 6.69, 7.07, 7.40, 7.55, 7.72, 8–14μ (broad band with peaks at 8.04, 8.7, 9.23, 10.37 and 12.75μ).

Anal. Calcd for C$_{12}$H$_{36}$N$_6$S$_3$O$_{12}$: C, 26.09; H, 6.57: N, 15.21; S, 17.38. Found: C, 26.04; H, 6.57; N, 15.27; S, 17.41.

A sample of the tris-dihydrosulfate salt was converted to the free base by treatment with 50% sodium hydroxide solution. The product was extracted into dichloromethane/tetrahydrofuran solvent and the solvent evaporated to leave 1,4,7,10,13,16-hexaazacyclooctadecane as a white solid. The product was purified by sublimation at 125° (0.1 mm), mp 149°–151°.

IR (KBr): 2.92, 3.12, 3.46, 3.56 (st), 3.76, 6.4, 6.61, 6.82, 6.96 (st), 7.31 (w), 7.49, 7.83, 8.08, 8.28, 8.51, 8.92 (st), 9.45, 10.56, 10.91, 11.31, 11.52, 12.18, 12.35 (st), 12.5, 12.83, and 13.08 μ (st). NMR (CDCl$_3$): 1.48 (broad s, 6H, NH) and 2.75 ppm (s, 24H).

Anal. Calcd for C$_{12}$H$_{30}$N$_6$: C, 55.78; H, 11.70; N, 32.52 Found: C, 55.55; H, 11.52; N, 32.11.

Mass spectrometry showed strong parent ion at m/e 258.2520 (calcd 258.2530) and ions at 214, 202, 190, 171, 159, 130 and 99. A peak at m/e 279, possibly an ion from a hydrate of hexaazacyclooctadecane was also seen.

EXAMPLE 5

1,4,7,10,13,16,19-Heptaazacycloheneicosane

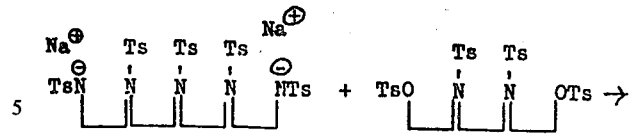

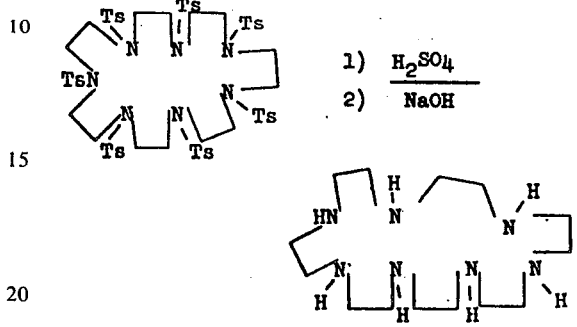

The above reaction on a 10-mmole scale in DMF using the procedure outlined in Example 1 gave 6.2 g (45% yield) of the heptatosylamide of 1,4,7,10,13,16,19-heptaazacycloheneicosane. This product was purified by recrystallization from acetonitrile, mp 183°–184°. IR (KBr): 3.3, 3.41, 6.24, 6.69, 6.87, 7.15, 7.44 (st), 7.65, 7.75, 8.45, 8.64 (st), 8.95, 9.17, 9.83, 10.2 (broad), 12.29, 13.5 (broad), 14.03, 14.4 and 15.2 μ. NMR (CDCl$_3$): 2.40 (broad s, 21H), 2.90 (DMF solvate doublet), 3.32 (broad s, 28H), and 7.2–7.8 ppm (m, 28H, aromatic).

Anal. Calcd for C$_{63}$H$_{77}$N$_7$S$_7$O$_{14}$: C, 54.82; H, 5.62; N, 7.10; S, 16.23. Found: C, 55.10; H, 5.61; N, 7.32; S, 16.62.

A 3.3-g sample of the heptatosylamide prepared as described above, was dissolved in 17 ml of concentrated sulfuric acid and the solution heated at 100° for 2 hours to remove the tosyl groups as described in Example 1. The dihydrosulfate salt was precipitated by the addition of 50 ml of ether at 25°. The off-white solid salt obtained was dissolved in water and the solution made basic with 20 ml of 50% sodium hydroxide solution, and the mixture was continuously extracted with benzene.

Evaporation of the benzene left 0.65 g of crude 1,4,7,10,13,16,19-heptaazacycloheneicosane, contaminated with 39% benzene as judged by nmr (55% yield of product). Further extraction of the basic solution with benzene gave an additional 0.19 g of product. The crude product was converted to its heptahydrochloride salt by treatment with 12N HCl in methanol. The crude hydrochloride salt obtained was recrystallized from water to give purified 1,4,7,10,13,16,19-heptaazacycloheneicosane heptahydrochloride as white needles, mp 280°–288° (dec). Anal. Calcd for (C$_2$H$_5$N.HCl)$_7$: C, 30.20; H, 7.60; N, 17.60; Cl, 44.60. Found: C, 30.57; H, 7.85; N, 17.53; Cl (Ionic), 43.50.

EXAMPLE 6

1,5,9,13-Tetraazacyclohexadecane

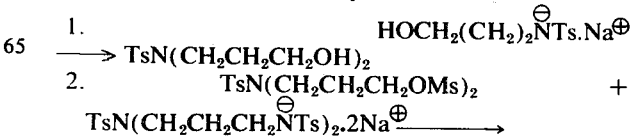

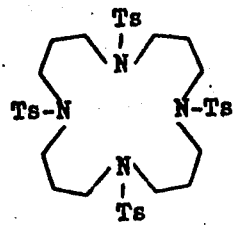

(3) 1) $H_2SO_4$
2) NaOH →

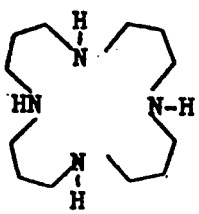

Ms = $CH_3SO_2$.

Reaction of 189 g of $HOCH_2(CH_2)_2\overset{\ominus}{N}Ts.\overset{\oplus}{Na}$ with 70 g of 3-chloropropanol in 1400 ml of DMF (nitrogen atmosphere) at 100° for 30 minutes gave, after separation of the DMF by distillation, 113 g of crude oily N,N-bis-(3-hydroxypropyl)-p-toluenesulfonamide. This product, dissolved in 2 liters of methylene chloride containing 160 ml of triethylamine, was treated at −20° with 62 ml of methanesulfonyl chloride. The reaction mixture was warmed to 0°, 1 liter of water was added, the organic phase was separated and washed successively with concentrated hydrochloric acid (50 ml), water (500 ml) and saturated sodium bicarbonate solution. After the methylene chloride was separated by distillation, 180 g of oily bis(methanesulfonate) derivative remained. To this product was added 225 g of $TsN(CH_2CH_2CH_2\overset{\ominus}{N}Ts)_2.2\overset{\oplus}{Na}$ in 2 liters of DMF and the reaction was carried out by warming this mixture to 60°–70° for 4 hours, then 100° for 0.5 hour. Workup as described in Example 1 gave, after recrystallization from chloroform, 143 g (22% overall yield) of the tetratosylamide of 1,5,9,13-tetraazacyclohexadecane of 90–95% purity (tlc).

The tetratosylamide was converted to the tetradihydrosulfate salt by treatment with concentrated sulfuric acid (100°; 3 hours) as described in Example 1. The product was isolated by addition of ether, and the crude product separated and washed with ethanol to give 1,5,9,13-tetraazacyclohexadecane tetra-dihydrosulfate salt as a white solid, weight 113 g. A solution of 48.1 g of this salt in 150 ml of water was treated with 100 g of 50% NaOH solution, and the product was extracted into benzene. Evaporation of the benzene and sublimation of the residue (120°, 0.5 mm) gave 10.3 g (58%) of white solid 1,5,9,13-tetraazacyclohexadecane, mp 84°–85.5°.

Anal. Calcd for $C_{12}H_{28}N_4$: C, 63.11; H, 12.36; N, 24.53. Found: C, 62.64; H, 12.02; N, 24.61.

EXAMPLE 7

Copper Complex of 1,4,7,10,13-Pentaazacyclopentadecane

Purified 1,4,7,10,13-pentaazacyclopentadecane (1.08 g, 5 mmole) was diluted to 50 ml with ethanol and 10 ml of this solution mixed with an ethanol solution of $CuCl_2.2H_2O$ (1 mmole). A deep blue color was formed immediately. The solvent was removed, benzene added and then removed by distillation to leave the copper complex as a deep blue solid. A sample of the complex, dissolved in water, was stable in 0.1N HCl, but disappearance of the blue color was noted upon addition of 10% hydrochloric acid. The complex was insoluble in benzene and acetonitrile.

EXAMPLE 8

Copper Complex of 1,4,7,10,13,16-Hexaazacyclooctadecane

A slurry of 2.75 g (5 mmoles) of the tridihydrosulfate salt of 1,4,7,10,13,16-hexaazacyclooctadecane in 50 ml of boiling water was dissolved by addition of 10 ml of 1N NaOH solution. To this solution was added a solution of 3.66 g (15 mmoles) $BaCl_2.2H_2O$ in 50 ml of water. The barium sulfate formed was digested in 0.5 hour, filtered and the filtrate treated with 50 ml of 0.1N $CuCl_2.2H_2O$ in ethanol (0.5 hour near reflux). The blue solution was neutralized with 19 ml of 1N NaOH solution, filtered, and the filtrate concentrated to dryness. The residue was dissolved in ethanol and the solution heated under reflux for a short time, filtered, and the ethanol removed to leave the crude copper complex as an oil. The product was purified by crystallization from ethanol-ether to give 1.5 g (76% yield) of the copper complex of 1,4,7,10,13,16-hexaazacyclooctadecane as blue prisms. Analysis indicated the complex contained a small amount of excess $CuCl_2$.

Anal. Calcd for $C_{12}H_{30}N_6CuCl_2$: C, 36.68; H, 7.70; N, 21.39; Cl, 18.05; Cu, 16.17. Found: C, 35.96; H, 7.06; N, 20.95; Cl, 19.70.

Similar complexes can be made with silver, gold, chromium, molybdenum, cadmium, mercury, manganese, iron, cobalt, nickel, ruthenium, or platinum by mixing an aqueous solution of salt of the selected metal with a solution of the hydrochloride or dihydrosulfate salt of the amine.

EXAMPLE 9

Copper Complexes of Monocyclic Polyamines

An aqueous solution of the polyamine hydrochloride or polyamine dihydrosulfate was treated with an equivalent of aqueous solution of $CuCl_2.2H_2O$. In each case the deep blue copper complex of the polyamine was formed in solution. The solution was then titrated with aqueous hydrochloric acid and the pH of the disappearance of the deep blue color noted. This pH corresponds to the decomposition of the copper complex, and the value indicates the relative stability of the complex in acidic solution. The results are tabulated in Table I.

TABLE I

| Polyamine | pH of Decomposition of Copper Complex |
|---|---|
| 1,4,7-Triazacyclododecane | 4.8–5.2 |
| 1,4,7,10,13,16-Hexaazacyclooctadecane | 1.3–2.0 |
| 1,4,7,13,16,19-Hexaazacyclotetracosane | 3.25–3.65 |
| 1,4,7,10,13-Pentaazacyclopentadecane | 0.3–0.75 |

EXAMPLE 10

Complexes of 1,4,7,10,13-Pentaazacyclopentadecane With Other Metals

When an ethanol solution of 1,4,7,10,13-pentaazacyclopentadecane was treated with ethanolic solutions of zinc chloride and nickel chloride as described in Example 7, the corresponding zinc and nickel complexes of the polyamine were formed. The complexes were isolated as described. The zinc complex of the polyamine was obtained as a white solid, and the solid nickel complex was deep lavender in color.

The use of metal complexes as curing agents for epoxy resins is shown in the following examples.

EXAMPLE A

A 222 mg sample of commercial epoxy resin (Dow Epoxy Resin 331) was mixed with 13 mg of the zinc complex of 1,4,7,10,13-pentaazacyclopentadecane. The clear mix was heated at 135°C for 2 hours and finally at 175°C for 5–10 minutes, then cooled. A light yellow, hard clear resin was obtained.

EXAMPLE B

The experiment of Example A was repeated using a stoichiometric quantity (131 mg) of the zinc complex with 275 mg of the epoxy resin. The opaque mix was heated at 135°C for 2 hours to give an opaque yellow, hard resin.

The embodiments of the invention in which an exclusive property or privilege is claimed are as follows:

1. A compound having the formula

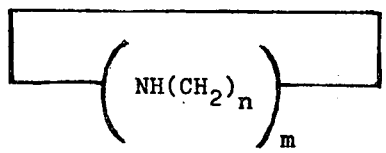

where $m$ is an integer of 3–7, and each $n$, independently, is an integer of 2–5, with the provisos that when $m$ is 3 and two of the $n$ values are 2 or 3, then the third $n$ is 4 or 5, and when $m$ is 4 and one $n$ is 2, then the remaining values of n are 3, 4 or 5.

2. The compound of claim 1 having the name 1,4,7-triazacyclododecane.

3. The compound of claim 1 having the name 1,4,7,13,16,19-hexaazacyclotetracosane.

4. The compound of claim 1 having the name 1,4,7,10,13-pentaazacyclopentadecane.

5. The compound of claim 1 having the name 1,4,7,10,13,16-hexaazacyclooctadecane.

6. The compound of claim 1 having the name 1,4,7,10,13,16,19-heptaazacycloheneicosane.

7. The compound of claim 1 having the name 1,5,9,13-tetraazacyclohexadecane.

* * * * *